(12) United States Patent
Crivello (10) Patent No.: US 6,828,404 B2
(45) Date of Patent: Dec. 7, 2004

(54) POLYMERIZABLE SILOXANES

(75) Inventor: James Vincent Crivello, Clifton Park, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 10/087,031

(22) Filed: Oct. 19, 2001

(65) Prior Publication Data

US 2002/0137870 A1 Sep. 26, 2002

Related U.S. Application Data

(60) Provisional application No. 60/241,887, filed on Oct. 20, 2000.

(51) Int. Cl.$^7$ .......................... C08G 77/06; C08G 77/12
(52) U.S. Cl. ............................. 528/25; 528/27; 528/31; 528/32; 528/33; 528/34; 556/445; 556/451; 556/466; 556/478; 556/479
(58) Field of Search .............................. 528/25, 27, 31, 528/32, 33, 34; 556/445, 451, 466, 478, 479

(56) References Cited

U.S. PATENT DOCUMENTS

| | | | |
|---|---|---|---|
| 5,019,607 A | | 5/1991 | Coltrain et al. ............. 523/435 |
| 5,035,894 A | | 7/1991 | Lee et al. .................... 424/448 |
| 5,316,695 A | | 5/1994 | Wilkes et al. ............ 252/315.6 |
| 5,344,905 A | * | 9/1994 | Morita ........................ 528/15 |
| 5,358,983 A | * | 10/1994 | Morita ....................... 523/455 |
| 5,484,950 A | * | 1/1996 | Crivello ...................... 549/215 |
| 5,650,474 A | | 7/1997 | Yamaya et al. ............... 528/12 |
| 6,011,079 A | | 1/2000 | Dougherty et al. ........... 528/12 |
| 6,251,990 B1 | * | 6/2001 | Meguriya et al. ........... 524/862 |

FOREIGN PATENT DOCUMENTS

EP  0 640 670 A2  3/1995  ......... C09D/183/04

OTHER PUBLICATIONS

Crivello, J., & Mao, Z., "Synthesis of Novel Multifunctional Siloxane Oligomers using Sol–Gel Techniques and Their Photoinitiated Cationic Polymerization," Chem. Mater., vol. 9, pp. 1554–1561, 1997.

Crivello, J., & Mao, Z., "Preparation and Cationic Photopolymerization of Organic–Inorganic Hybrid Matrixes," Chem. Mater., vol. 9, pp. 1562–1569, 1997.

Crivello, J., Yang, B. & Whan–Gi, K., "Synthesis and Electron–Beam Polymerization of 1–Propenyl Ether Functional Siloxanes," Pure Appl. Chem., vol. A33(4), pp. 399–415, 1996.

Crivello, J., & Löhden, G., "Synthesis and Photopolymerization of 1–Propenyl Ether Functional Siloxanes," Chem. Mater., vol. 8, pp. 209–218, 1996.

Acrylic and Methacrylic Ester Polymers "Encyclopedia of Polymer Science and Engineering", vol. 1, pp. 274–275.

* cited by examiner

Primary Examiner—Jeffrey B. Robertson
(74) Attorney, Agent, or Firm—Heslin Rothenberg Farley & Mesiti P.C.; Mary Louise Gioeni, Esq.

(57) ABSTRACT

A process for the preparation of an alkoxysilyl siloxane substituted with at least one epoxy, vinyl ether, 1-propenyl ether, acrylate or methacrylate group comprises selectively reacting a hydrosilane compound with a compound containing a vinyl or allyl group and a epoxy, vinyl ether, 1-propenyl ether, acrylate or methacrylate group, or a compound containing at least one vinyl or allyl group and at least one dialkoxysilyl or trialkoxysilyl group, to form at least one monohydrosiloxane. The monohydrosiloxane is further reacted to form an ambifunctional alkoxysilyl siloxane.

13 Claims, 8 Drawing Sheets

POLYMERIZABLE SILOXANES

CROSS-REFERENCE TO RELATED APPLICATIONS

This application claims priority from U.S. Provisional Application, Ser. No. 60/241,887, filed on Oct. 20, 2000.

FIELD OF THE INVENTION

The invention relates to a process for the preparation of polymerizable alkoxysilyl siloxanes.

BACKGROUND OF THE INVENTION

In recent years, organic-inorganic hybrid resins have received much attention in the literature due to their unique electrical, optoelectronic and mechanical properties. Much work is currently focused on the synthesis of crosslinked glass-like matrices composed of Si—O—Si linkages employing sol-gel techniques that involve the acid or base catalyzed hydrolysis of tri- or tetra-alkoxysilanes. The resulting organic-inorganic hybrid resins have many potential applications, including nonstick release coatings, adhesives, abrasion-resisting coatings for plastics, fiber optic coatings, reinforced composites and optical wave guides. However, traditional sol-gel techniques for their synthesis have a number of drawbacks which have limited their use. First, sol-gel chemistry is slow, often requiring days or weeks for the hydrolysis of the alkoxysilane to proceed to completion. Second, during hydrolysis and subsequent condensation of the resulting silanols, a highly porous, crosslinked matrix resin is formed. If the hydrolysis is carried out too rapidly, the fragile matrix can fracture. Third, during the hydrolysis, there is always considerable shrinkage of the resin matrix. Densification of the initially formed porous matrix by calcination is often required to produce specimens with good cohesive and mechanical strength. Finally, the modification of sol-gel matrices through the incorporation of functionalized alkoxysilane precursors is sometimes difficult, due to the difference in the hydrolysis rates of the components or to their phase separation during the cohydrolysis step.

U.S. Pat. No. 6,069,259 describes a process for the production of an oligomeric alkoxysiloxane substituted with functional groups, including epoxy or 1-alkenyl ether. In the process, hydrolysis/condensation of a trialkoxysilane bearing functional groups is catalyzed by an ion exchange resin (IER).

The process yields resins with high reactivity and low volatility that can be prepared with controllable molecular weights. One drawback to the process is the high intrinsic cost of the starting materials. Accordingly, there is a need for a streamlined, lower cost process for the production of functionalized siloxane monomers and oligomers.

SUMMARY OF THE INVENTION

A new generally applicable synthetic approach that can be employed to prepare a family of silicone-epoxy resins using simple, readily available precursors has been unexpectedly discovered. These resins undergo facile cationic photopolymerization to yield organic-inorganic hybrid resins with a wide range of properties.

Accordingly, in one aspect, the present invention relates to a process for the preparation of an alkoxysilyl silane or siloxane containing at least one polymerizable functional group selected from epoxy, vinyl ether, 1-propenyl ether, acrylate and methacrylate. The process comprises selectively reacting at least one compound of formula I with at least one compound chosen from A or B, to form a monohydrosilane or monohydrosiloxane; and reacting the monohydro compound with at least one compound chosen from A and B, to form an alkoxysilyl silane or siloxane, with the proviso that when A is used in step (a), B is used in step (b), and when B is used in step (a), A is used in step (b). A is defined as a compound containing at least one vinyl or allyl group and at least one group selected from epoxy, vinyl ether, 1-propenyl ether, acrylate and methacrylate; B is a compound containing at least one vinyl or allyl group and at least one dialkoxysilyl or trialkoxysilyl group; and $R^1$–$R^4$ are independently hydrogen, alkyl, haloalkyl, arylalkyl, aryl or heterocyclic; and n is 0 or an integer from 1 to 100.

In another aspect, the invention relates to a process for the preparation of an alkoxysilyl silane or siloxane substituted with a polymerizable epoxy, vinyl ether, 1-propenyl ether, acrylate or methacrylate group. The process comprises forming an alkoxysilyl silane or siloxane, as described above; and, in the presence of an ion exchange resin, reacting 0.5 to 2.5 equivalents water with the alkoxysilyl compound; and separating the ion exchange resin from a product of the reaction.

In the context of the present invention, alkyl is intended to include linear, branched, or cyclic hydrocarbon structures and combinations thereof. Lower alkyl refers to alkyl groups of from 1 to 4 carbon atoms. Lower alkyl groups include methyl, ethyl, n-propyl, isopropyl, and n-, s- and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Aryl and heteroaryl mean a 5- or 6-membered aromatic or heteroaromatic ring containing 0–3 heteroatoms selected from nitrogen, oxygen or sulfur; a bicyclic 9- or 10-membered aromatic or heteroaromatic ring system containing 0–3 heteroatoms selected from nitrogen, oxygen or sulfur; or a tricyclic 13- or 14-membered aromatic or heteroaromatic ring system containing 0–3 heteroatoms selected from, oxygen or sulfur. Each of these rings is optionally substituted with 1–3 lower alkyl, substituted alkyl, substituted alkynyl, carbonyl, nitro, halo, haloalkyl, hydroxy, alkoxy, OCH(COOH)$_2$, cyano, primary amino, secondary amino, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substitutents selected from lower alkyl, alkenyl, alkynyl, halogen, hydroxy, haloalkyl, alkoxy, cyano, phenyl, benzyl, benzyloxy, carboxamido, heteroaryl, heteroaryloxy, nitro or —NRR (wherein R is independently H, lower alkyl or cycloalkyl, and —RR may be fused to form a cyclic ring with nitrogen). The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples are benzyl and phenethyl. Heteroarylalkyl means an alkyl residue attached to a heteroaryl ring. Examples include pyridinylmethyl and pyrimidinylethyl.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, aryl, cycloalkyl, or heterocyclyl refer to alkyl, aryl, cycloalkyl, or heterocyclyl wherein up to three H atoms in each residue are replaced with halogen, haloalkyl, hydroxy, lower alkoxy, carboxy, carboalkoxy, carboxamido, cyano, carbonyl, nitro, primary amino, secondary amino, alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

DETAILED DESCRIPTION OF THE INVENTION

The present invention relates to a process for the preparation of silane and siloxane compounds substituted with at least one polymerizable functional group selected from epoxy, vinyl ether, 1-propenyl ether, acrylate and methacrylate. In the process, at least one silane or siloxane compound of Formula I where $R^1$–$R^4$ are, independently, hydrogen, alkyl, haloalkyl, arylalkyl, aryl or heterocyclic, and n is zero or an integer from 1 to 100, is initially and selectively reacted with at least one vinyl or allyl compound containing a polymerizable functional group selected from epoxy, vinyl ether, 1-propenyl ether, acrylate and methacrylate or an alkoxysilyl group, designated A or B, respectively, to form a monohydrosilane or monohydrosiloxane. If desired, the intermediate may be isolated and characterized as described in U.S. Pat. No. 5,484,950; it is, however, typically advantageous to proceed to the next step without isolating. A second vinyl or allyl compound(s), containing an alkoxysilyl group or a polymerizable functional group, B or A, is then reacted with the monohydro compound to form a silane or siloxane containing both a polymerizable functional group and an alkoxysilyl group. The process is illustrated in Scheme 1, for the case where I is 1,1,3,3-tetramethyldisiloxane, A is 3-vinyl-7-oxabicyclo[4.1.0] heptane and B is vinyltrimethyoxysilane.

Scheme 1

-continued

Thus, in a simplified, one-pot process, compounds bearing both trialkoxysilyl and polymerizable functional groups can be readily prepared in high yield.

A is defined as a compound containing at least one vinyl or allyl group and at least one polymerizable functional group selected from epoxy, vinyl ether, 1-propenyl ether, acrylate and methacrylate. B is defined as a compound containing at least one vinyl or allyl group and at least one dialkoxysilyl or trialkoxysilyl group. These compounds undergo facile hydrosilation only at the vinyl or allyl site. It should be noted that where A is reacted with I initially, the resulting monohydrosiloxane is reacted with B in the second step. Conversely, where B is used in the first step, A is used in the second step.

A may be more narrowly defined as a compound comprising a linear, branched or cyclic alkyl or alkyl ether residue having 1–20 carbon atoms, or 1–20 carbon atoms and 1–9 oxygen atoms, and substituted with at least one vinyl or allyl group and at least one group selected from epoxy, vinyl ether, 1-propenyl ether, acrylate and methacrylate. Examples of compounds which may be used as component A are shown in Table 1.

TABLE 1

In particular, A may be 3-vinyl-7-oxabicyclo [4.1.0] heptane.

B may be more narrowly defined as an alkoxysilane of formula II wherein
  $R^7$ is a direct bond or a divalent aryl or alkyl residue; and
  $R^8$, $R^9$, and $R^{10}$ are independently alkyl, aryl, arylalkyl, chloroalkyl, fluoroalkyl, heteroalkyl, heteroaryl, alkoxy, arylalkoxy, chloroalkoxy, or fluoroalkoxy. Examples of compounds which may be used as component B are shown in Table 2.

TABLE 2

In particular, B may be vinyltrimethoxysilane.

In another embodiment, the present invention relates to a process for the preparation of polymerizable silane or siloxane oligomers. The process includes preparing at least one silane or siloxane compound having a terminal alkoxysilyl group and an epoxy, vinyl ether, 1-propenyl ether, acrylate or methacrylate group, as described above. Condensation of I with at least one compound chosen from A and B, yields at least one monohydrosilane or monohydrosiloxane, which is then reacted with at least one compound chosen from A and B, to form an alkoxysilyl silane or siloxane. As before, the compound may be isolated and fully characterized, or it may be directly carried through to the next step. In this step, alkoxysilyl groups are condensed with 0.5–2.5 equivalents water in the presence of an ion exchange resin. If desired, all three reactions may be carried out in a sequential fashion in a one-pot reaction. Alternatively, the reaction sequence may be run in a step-by-step fashion with the isolation of the products after any reaction step.

If desired, an alkoxysilane of formula $SiR^6R^8R^9R^{10}$ may be included in the IER-catalyzed condensation reaction; $R^6$, $R^8$, $R^9$, and $R^{10}$ are independently alkyl, aryl, arylalkyl, chloroalkyl, fluoroalkyl, heteroalkyl, heteroaryl, alkoxy, arylalkoxy, chloroalkoxy, or fluoroalkoxy of 1 to 10 carbons. In particular, $R^6$, $R^8$, $R^9$, and $R^{10}$ may be independently chosen from methyl, methoxy, ethyl, ethoxy, and phenyl. Examples of useful alkoxysilane comonomers tetraethoxysilane (ethylorthosilicate), tetramethoxysilane (methylorthosilicate), tetraisopropoxysilane, methyltrimethoxysilane, ethyltriethoxysilane, hexyltriethoxysilane, cyclohexyltrimethoxysilane, 1,1,1-trifluoroethyltriethoxysilane, phenyltriethoxysilane, phenylmethyldiethoxysilane, phenylmethyldimethoxysilane, diphenyldimethoxysilane, 2-phenylethyltrimethoxysilane, benzyltriethoxysilane, vinyltrimethoxysilane, dimethyldimethoxysilane, trimethylmethoxysilane, diethyldimethoxysilane, allyltrimethoxysilane, divinyldimethoxysilane, methyvinyldimethoxysilane, bis(triethoxysilyl)methane, bis(triethoxysilyl)ethane, butenyltrimethoxysilane, 3-bromopropyltrimethoxysilane, 2-chloroethylmethyldimethoxysilane, 1,1,2,2-tetramethoxy-1,3-dimethyldisiloxane, phenyltrimethoxysilane. Also, useful in these mixtures are trimethoxysilyl-terminated polydimethylsiloxanes as well as the corresponding hydroxyl-terminated polydimethylsiloxanes. These coreactants are either commercially available or readily synthesized by reactions well known in the art.

An alkoxysilane of formula $SiR^8R^9R^{10}$ FG, bearing a polymerizable functional group, may also be included in the IER-catalyzed condensation step; $R^6$, $R^8$, $R^9$, and $R^{10}$ are defined above, and FG is a linear, branched or cyclic alkyl or alkyl ether residue of 1–20 carbon atoms, or 1–20 carbon atoms and 1–9 oxygen atoms, substituted with at least one group selected from epoxy, vinyl ether, 1-propenyl ether, acrylate and methacrylate. Some examples of such alkoxysilanes are shown in Table 3.

TABLE 3

Epoxy Functional Silicone Resins

| Notation | Structure | Yield (%) | Viscosity (cP) | Mw (g/mol) | MWD | DP |
|---|---|---|---|---|---|---|
| Ib | [structure] | 100 | 2506 | 2430 | 1.3 | 9 |

TABLE 3-continued

Epoxy Functional Silicone Resins

| Notation | Structure | Yield (%) | Viscosity (cP) | Mw (g/mol) | MWD | DP |
|---|---|---|---|---|---|---|
| VIIb |  | 92 | 33260 | 2381 | 1.1 | 6 |
| VIIIb |  | 98 | 2929 | 4186 | 1.3 | 9 |
| IXb |  | 95 | 648 | 6440 | 1.4 | 11 |

TABLE 3-continued

Epoxy Functional Silicone Resins

| Notation | Structure | Yield (%) | Viscosity (cP) | Mw (g/mol) | MWD | DP |
|---|---|---|---|---|---|---|
| Xb | (structure) | 93 | 249 | 8135 | 1.7 | 9 |

†under pressure

The amount of alkoxysilane coreactant of formula $SiR^6R^8R^9R^{10}$ or $SiR^8R^9R^{10}$ FG may range from 5–90%, based on the total weight of silyl and silane co-reactants. In particular, 25–70% of the coreactant may be used.

The ion exchange resin catalyzed sol-gel polycondensation reaction can be conducted in various solvents, however, alcohols such as ethanol, t-butanol, n-propanol or isopropanol alone or in combinations with water are preferred. Reaction can be conducted at room temperature or at elevated temperatures up to 170° C. with the application of pressure. The reaction is catalyzed by ion exchange resins containing quaternary ammonium functionality. Examples of ion exchange resins include Amberlite A-27, Amberlite IRA-400 and Amberlite IRA-904 from Rohm and Haas Co.

Most advantageously, the ion exchange resin is in a crosslinked bead form that permits easy recovery from the reaction mixture by simple filtration. The ion exchange resin hydrolysis catalyst may be reused in subsequent sol-gel reactions. Alternatively, the condensations may be carried out in a continuous fashion on a fixed bed of the resin. One of the major advantages of these catalysts for this purpose is that they may be easily and quantitatively removed by simple filtration after the sol-gel reaction so that no acidic or basic residues remain to inhibit the subsequent photoinduced cationic polymerization. In addition, excellent control over the complex sol-gel chemistry may be exercised with these catalysts. The reaction may be terminated at any stage of the reaction by removal of the catalyst. This prevents the reaction from proceeding further and gives multifunctional monomers and oligomers with excellent shelf-life and reproducible molecular weights and viscosities. Lastly, this chemistry is broadly adaptable for the preparation of tailor-made siloxanes with well-defined molecular weights, viscosities and including various reactive, polymerizable pendant functional groups. Reaction may be effected at any temperature up to the boiling point of the solvent used. Reactions may also be carried out at higher temperatures than the boiling point of the solvent with application of pressure.

After removal of the solvent, the resulting multifunctional siloxane oligomers may be polymerized by various means. For example, the epoxy functional oligomers may be combined with amine or anhydride curing agents and polymerized by traditional thermal methods. Acrylate and methacrylate functional oligomers may be similarly thermally cured through the use of conventional peroxide, azo, or metal-containing free radical initiators. Alternatively, these resins may be also free radical photopolymerized employing, for example, benzoin alkyl ethers, acylphosphine oxides, 1,1-diethoxyacetopheone, 1-benzoylcyclohexanol and the like as photoinitiators. Epoxy, 1-propenyl ether, 1-butenyl ether, oxetane and vinyl ether functional oligomers can be photopolymerized using UV or visible light irradiation in the presence of diaryliodonium, dialkylphenacylsulfonium, triarylsulfonium salt, and ferrocenium salt photoinitiators. The aforementioned resin-photoinitiator mixtures may be also effectively cured in the presence of the above onium salts using e-beam or $^{60}$Co gamma ray irradiation.

Materials produced by the process of the invention have many applications. The precursors to the sol-gel condensation can be employed as coupling agents to promote adhesion between various substrates, as for example, between glass fibers and an epoxy resin. Such coupling agents are widely used in the composites and reinforced plastic industries. The polymerizable siloxane oligomers resulting from IER-catalyzed condensation of II may be employed as protective and abrasion resistant coatings for wood metals, plastics and glass. They may be employed as adhesive or bonding agents. Combined with fibrous reinforcing agents they may be cured by UV and e-beam radiation to give high performance composites. They may be further used as curable encapsulating and potting agents for electronic and microelectronic applications. Further uses lie in resins for stereolithography, holographic recording and as optical adhesives, fiber optic coatings and wave guides in photonic applications. In the course of their use in various applications, the resins may be combined with various fibrous or particulate reinforcing agents, flow control and flatting agents, photosensitizers, pigments and dyes and mold releases.

EXAMPLES

Figure 1:
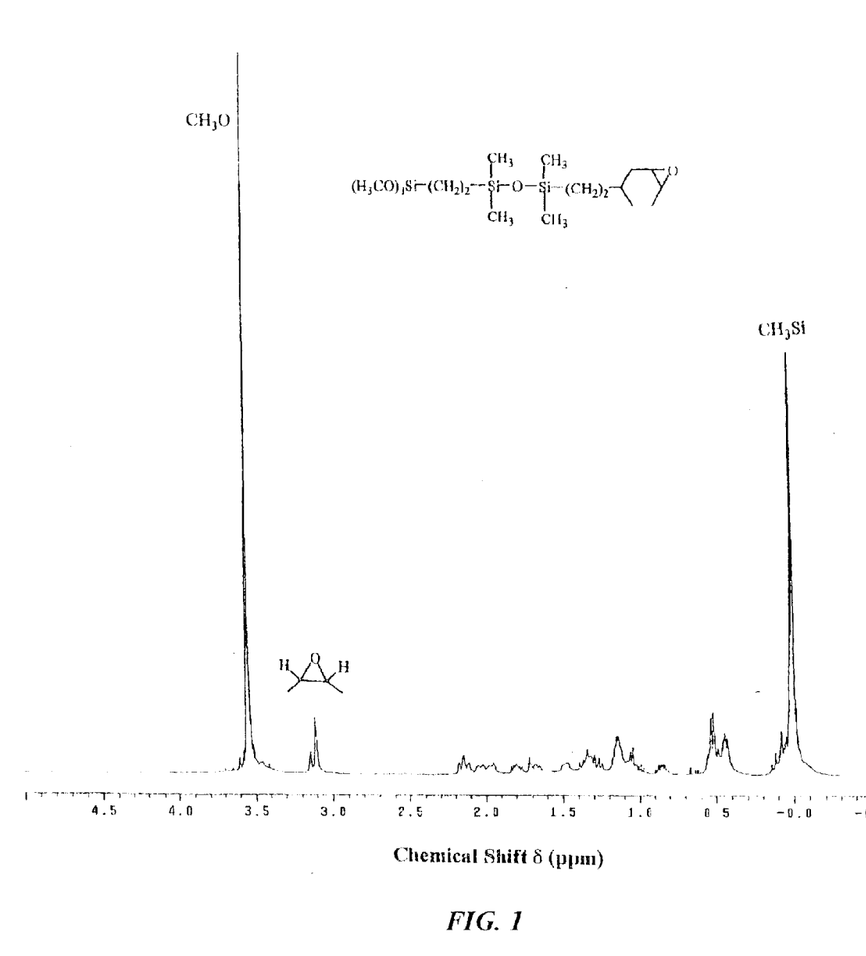
FIG. 1 is a $^1$H-NMR spectrum of the ambifunctional sol-gel precursor of Example 1, 1-[2-(3-(7-oxabicyclo [4.1.0]heptyl)ethyl]-3-[2-trimethoxysilylethyl]-1,1,3,3-tetramethyldisiloxane (VIIIa).

General synthesis of a-epoxy-w-trialkoxysilanes and siloxanes given in Table I are the structures and elemental analyses of ambifunctional precursor compounds prepared. In FIG. 1 is shown a representative $^1$H-NMR spectrum of ambifunctional sol-gel precursor VIIIa.

The synthetic procedures given in Example 1 are typical of those used for the preparation all of the α-epoxy-ω-trialkoxysilanes and siloxanes herein.

Example 1

Preparation of 1-[2-(3-(7-Oxabicyclo[4.1.0]heptyl) ethyl]-3-[2-trimethoxysilylethyl]-1,1,3,3-tetramethyldisiloxane (VIIIa)

A mixture of 20.0 g (0.15 mol) of distilled 1,1,3,3-tetramethyldisiloxane, 18.5 g (0.15 mol) of 3-vinyl-7-oxabicyclo[4.1.0]heptane, 20 mL of dry toluene were charged into 250-mL round bottom flask fitted with a reflux condenser and thermometer. There were added 30 mg of Wilkinson's catalyst, and the reaction mixture was heated at 60° C. for 4 h in an oil bath. After this time, the $^1$H-NMR spectrum showed that the vinyl peaks at 5.5 ppm had disappeared. Next, there were added 22.2 g (0.15 mol) of distilled vinyltrimethoxysilane. After 6 hours at 90° C., the infrared absorption at 2160 cm$^{-1}$ (Si—H group) had completely disappeared. Removal of the solvent under reduced pressure gave the desired product, (54, 6 g, 90% yield) of colorless oil, which was characterized by $^1$H-NMR and confirmed to be monomer VIIIa.

Preparation of Epoxy Functional Oligomers

The synthetic procedures given below are typical of those used for the preparation all of the silicone epoxy oligomers shown in Table 3.

Example 2

Sol-Gel Condensation of 2-(3,4-Epoxycyclohexylethyl)trimethoxysilane

A mixture of 20 g (0.081 mol) of Ia, 4.4 g (0.24 mol) of deionized water, 0.8 g of Amberlite IRA-400 ion exchange resin and 10 g of isopropanol were placed in a 100 mL round-bottom flask equipped with a magnetic stirrer and a reflux condenser. The condensation reaction was carried out at the reflux temperature, 82° C., for 6 hours. Thereafter, the solution was cooled, filtered and passed though a silica gel column using ethyl acetate as the eluent. The solvent was removed under vacuum, and a viscous liquid oligomer (16.3 g) Ib was obtained.

$^1$H-NMR (CDCl$_3$) d(ppm) 0.5, CH$_2$—Si; 1.2–2.2, aliphatic protons; 3.1, epoxy CH; 3.48, OCH$_3$.

Example 3

Sol-Gel Condensation of 2-(3-(7-Oxabicyclo[4.1.0] heptyl)ethyl-[2-trimethoxysilylethyl]-methylphenylsilane (VIIa)

A mixture of 6.0 g (0.015 mol) of VIIa, 0.82 g (0.0456 mol) of deionized water, 0.24 g of Amberlite IRA-400 ion exchange resin and 3.0 g of n-propanol were placed in a 100 mL round-bottom flask equipped with a magnetic stirrer and a reflux condenser. The hydrolysis-condensation reaction was carried out at the reflux temperature, 97° C., for 24 hours. After the solution was filtered and passed though a silica gel column using ethyl acetate as the eluent. The ethyl acetate was removed in vacuum and a viscous liquid oligomer (4.9 g) VIIb was obtained.

$^1$H-NMR (CDCl$_3$) d(ppm) 0.2–2.2, CH$_2$—Si and CH$_3$—Si and aliphatic protons; 3.1, epoxy CH; 3.48, OCH$_3$; 7.4, aromatic protons.

Example 4

Sol-Gel Condensation of 1-[2-(3-(7-Oxabicyclo [4.1.0]heptyl)ethyl]-3-[2-trimethoxy-silylethyl]-1,1,3,3-tetramethyldisiloxane (VIIIa)

To a 75 mL pressure vessel fitted with a magnetic stirrer were charged log (24.6 mmol) of VIIIa, 1.33 g (73.8 mmol) of deionized water, 0.4 g of Amberlite IRA-400 ion-exchange resin, and 5.0 g of isopropanol. The reaction mixture was stirred and heated at 150° C. for 12 hours under pressure. After the solution was filtered and passed though a silica gel column using ethyl acetate as the eluent, the solvent was removed in vacuum to give a viscous liquid oligomer VIIIb (8.4 g).

$^1$H-NMR (CDCl$_3$) d(ppm) 0–0.1, CH$_3$—Si; 0.5, CH$_2$—Si; 1.2–2.2, aliphatic protons; 3.1, epoxy CH; 3.4–3.8, OCH$_3$.

Example 5

Sol-Gel Condensation of 1-[2-(3-(7-Oxabicyclo [4.1.0]heptyl) ethyl]-5-[2-trimethoxy-silylethyl]-1,1,3,3,5,5-hexamethyltrisiloxane (IXa)

In a similar fashion to that described above, 10 g (20.1 mmol) of IXa, 1.12 g (62.2 mmol) of deionized water, 0.4 g of Amberlite IRA-400 ion-exchange resin, and 5.0 g of isopropanol were heated together at 150° C. for 12 hours in a pressure vessel. After workup as before, there were isolated 8.6 g of the desired oligomer as a viscous, colorless liquid IXb.

$^1$H-NMR (CDCl$_3$) d(ppm) 0–0.1, CH$_3$—Si; 0.5, CH$_2$—Si; 1.2–2.2, aliphatic protons; 3.1, epoxy CH; 3.4–3.8, OCH$_3$.

Example 6

Sol-Gel Condensation of 1-[2-(3-(7-Oxabicyclo [4.1.0]heptyl)ethyl]-7-[2-trimethoxysilylethyl]-1,1,3,3,5,5,7,7-octamethyltetrasiloxane (Xa)

In a similar fashion to that described above, 10 g (18.0 mmol) of Xa, 0.97 g (54 mmol) of deionized water, 0.4 g of Amberlite IRA-400 ion-exchange resin, and 5.0 g of isopropanol were heated together at 150° C. for 12 hours in a pressure vessel. After workup as before, there were isolated 8.55 g of the desired oligomer Xb as a viscous, colorless liquid.

$^1$H-NMR (CDCl$_3$) d(ppm) 0–0.1, CH$_3$—Si; 0.5, CH$_2$—Si; 1.2–2.2, aliphatic protons; 3.1, epoxy CH; 3.4–3.8, OCH$_3$.

Figure 2:
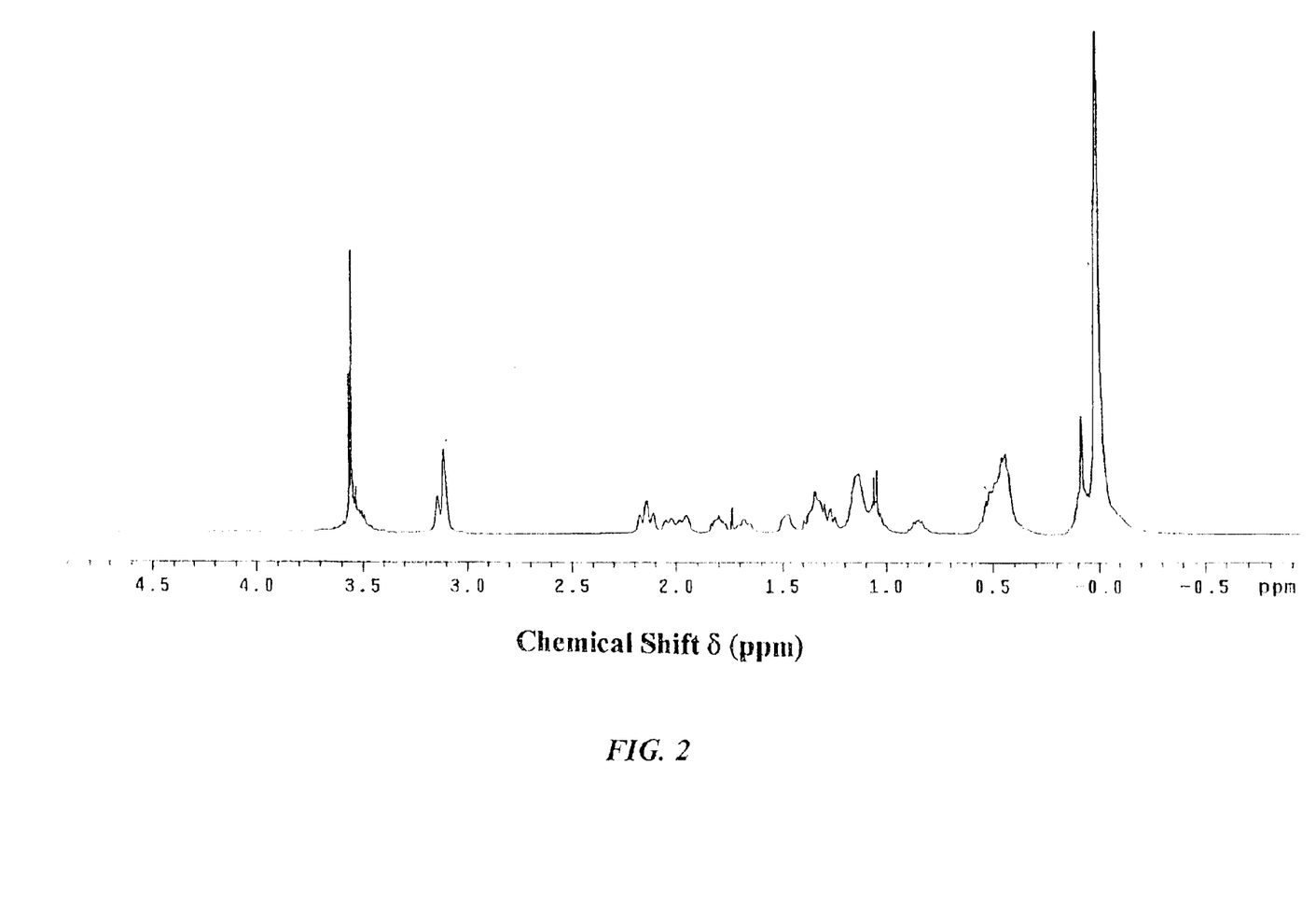
FIG. 2 is a $^1$H-NMR spectrum of the silicone epoxy oligomer (VIIIb) of Example 4.
Figure 3:
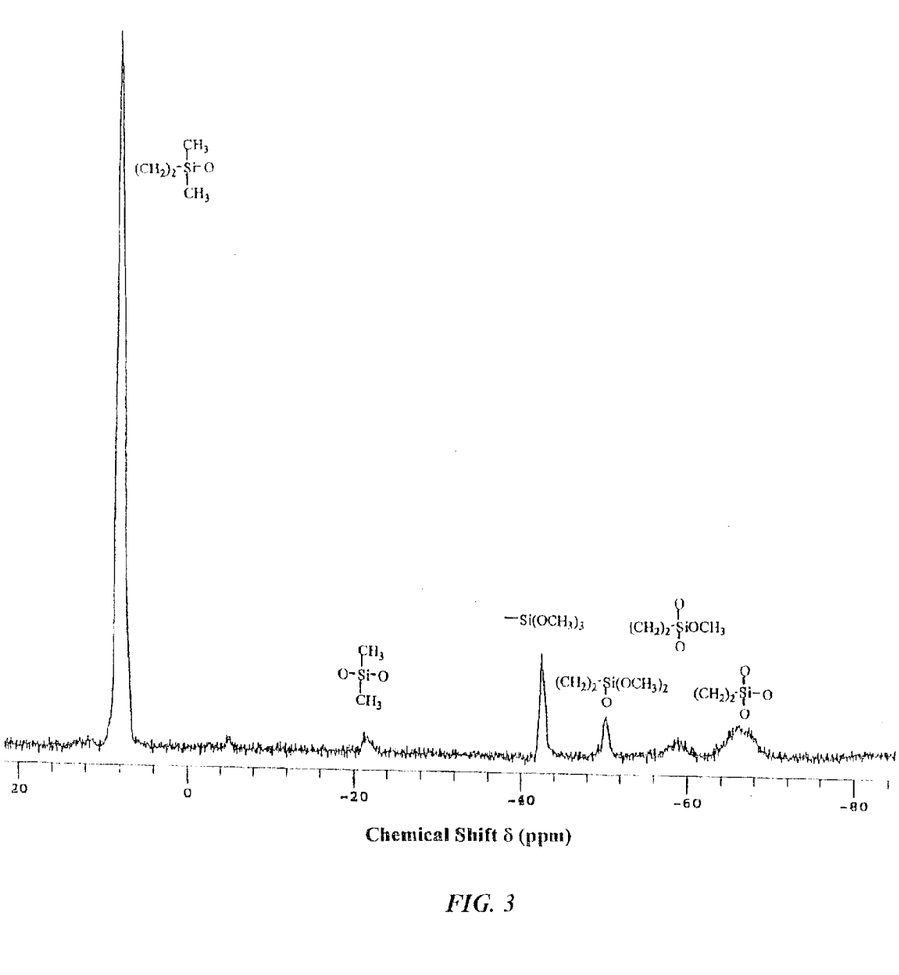
FIG. 3 is a $^{29}$Si-NMR spectrum of silicone epoxy oligomer VIIIb.

The sol-gel condensations of ambifunctional adducts Ia. and VIIa-Xa (eq. 5) proceed smoothly in the presence of water and a weakly acidic ion-exchange resin. Typically, the condensations were carried out in solution in either hot isopropanol or n-propanol. The reactions were usually terminated when greater than 85% of the methoxy groups (3.55 ppm) had undergone reaction as determined by $^1$H-NMR. It was found that as the siloxane chain of the spacer is lengthened, increasingly more vigorous conditions for the sol-gel reaction were required. Thus, while Ia undergoes sol-gel condensation in 6 h in isopropanol at 82° C., Xa, required 12 h heating at 150° C. under pressure in a sealed vessel. The desired silicone-epoxy oligomers were obtained as colorless viscous oils by filtering the reaction mixture to remove the ion-exchange resin and then stripping off the solvent under reduced pressure. Under these conditions ring-opening of the epoxy groups was not observed. The resulting silicone-epoxy oligomers were colorless to very pale yellow viscous liquids that displayed high reactivity in photo- and thermally initiated cationic polymerization. In FIG. 2 is shown the $^1$H-NMR spectrum of silicone-epoxy oligomer VIIIa. The $^{29}$Si-NMR for this same oligomer is shown in FIG. 3. Resonances corresponding to silicon atoms in six different types chemical environments are seen in the spectrum and are assigned as noted in FIG. 3. Together, these two spectra suggest a structure analogous to the proposed structure for oligomer II in which various degrees of hydrolysis of the trialkoxysilyl groups has taken place. Collected in Table 3 are the structures of the oligomers together with the conditions of their sol-gel condensations as well as the molecular weight and viscosity data. Again, it should be noted that the structures of the oligomers shown in Table 3 are idealized and that, in fact, the actual structure is much more complex with both cyclic and linear siloxane repeat units in the backbone. The approximate degree of polymerization (DP) is also given in Table 3. The oligomers range from hexamers to undecamers implying that they correspondingly possess on the average from six to eleven reactive epoxycyclohexyl groups per molecule. It is interesting to note that the viscosity of the oligomers appears to be closely related to the structure of the oligomers. Oligomer VIIb with aromatic groups has a high viscosity although the molecular weight is comparatively low due to increased rigidity caused by the introduction of the phenyl groups into the chain. As one increases the length of the dimethylsiloxane spacer in the resin, the viscosity decreases.

Example 7

Photopolymerization Studies Using Fourier Transform Real-Time Infrared Spectroscopy (FT-RTIR)

Photopolymerizations of all the monomers and oligomers in this work were monitored using Fourier Transform real-time infrared spectroscopy (FT-RTIR). A Midac—1300 FTIR spectrometer (Midac Corp., Irvine, Calif.) equipped with a liquid nitrogen cooled mercury-cadmium-telluride detector was used. The instrument was fitted with a UVEXS Model SCU-110 mercury arc lamp (Sunnyvale, Calif.) equipped with a flexible liquid optic wand. The end of this wand was placed at a distance of 5 cm and directed at an incident angle of 45° onto the sample window. UV light intensities were measured with the aid of a UV Process Supply, Inc. radiometer (Chicago, Ill.) at the sample window.

Photopolymerizations were carried out at room temperature using broadband UV light with an intensity of 6.7 mW/cm$^2$ in solutions of the epoxide monomers containing 2.0 mol % of IOC10 as the photoinitiator. The monomer/photoinitiator solutions were coated onto a 12 mm oriented and corona treated polypropylene film (General Electric Capacitor Dept., Hudson Falls, N.Y.), covered with an identical polypropylene film, and then mounted in 5 cm×5 cm slide frames. The thickness of the liquid monomer films was estimated at 10–25 mm. Infrared spectra were collected at a rate of 1 spectrum per second using LabCalc, data acquisition software obtained from the Galactic Industries Corp. (Salem, N.H.) and were processed using GRAMS-386 software from the same company. During irradiation, the decrease in the absorbance band due to the epoxy groups at 886 cm$^{-1}$ of the respective oligomers were simultaneously monitored. Data reduction and subsequent conversion versus time plots were obtained using Excel (Microsoft Corp. Redmond, Wash.) software. Three to five photopolymerization runs were performed for each kinetic study and the results averaged.

Photo- and Thermally Initiated Cationic Polymerization

Monomers bearing epoxycyclohexyl groups, in general, and silicone-epoxy monomers containing these groups, in particular, display high reactivity in photoinitiated cationic polymerization. The multifunctional sol-gel silicone-epoxy oligomers prepared in this investigation similarly undergo facile photo- and thermally induced cationic ring-opening polymerization in the presence of photosensitive onium salts. As noted above, (4-n-decyloxyphenyl) phenyliodonium hexafluoroantimonate (IOC10) was employed as both the thermal and photoinitiator for the cationic ring-opening polymerization of the epoxide groups. The structure of IOC10 is given below.

IOC10

Figure 4:
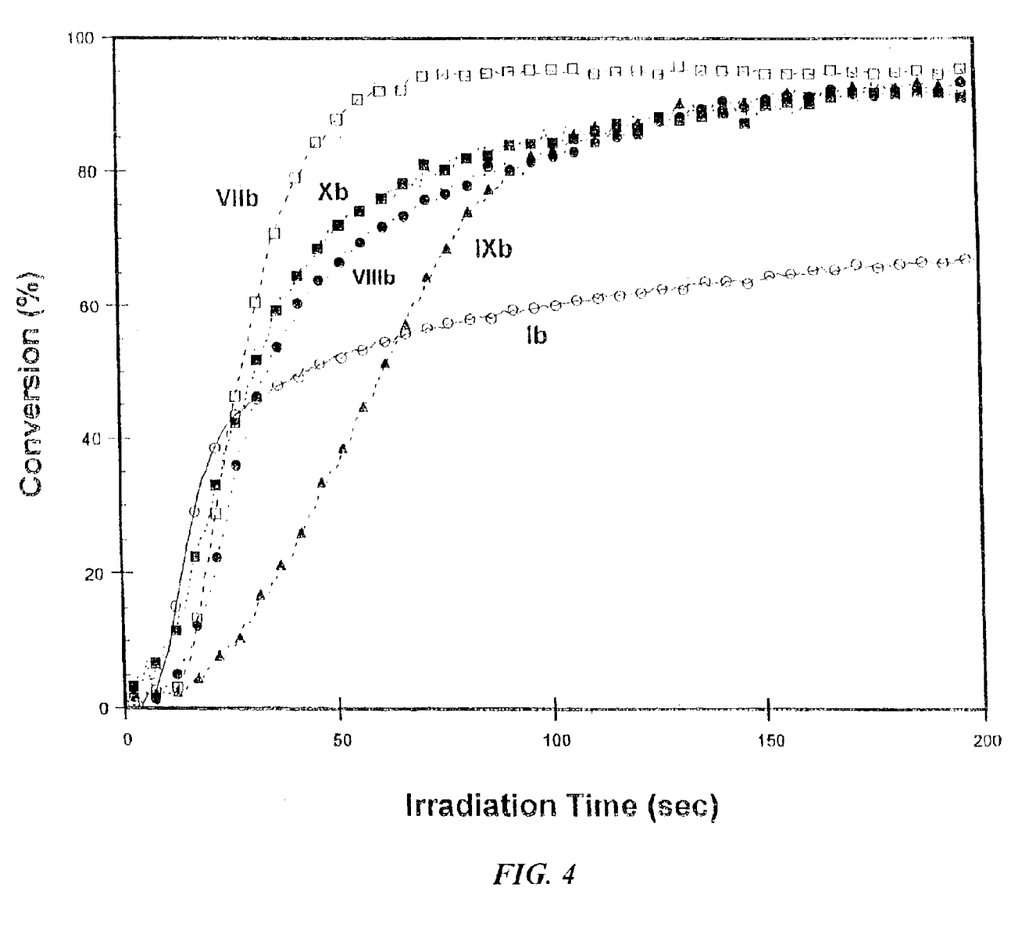
FIG. 4 shows a real-time infrared study of the cationic photopolymerization of silicone-epoxy oligomeric resins using 2.0 mol % of IOC10 as photoinitiator.
Legend: (○), Ib; (□), VIIb; (●), VIIIb; (▲), IXb; (■), Xb.

This compound was selected for its high solubility in all the silicone-epoxy oligomeric resins and because this onium salt has a high quantum yield (~0.7) and is a very efficient photoinitiator for the cationic ring-opening polymerization of epoxides. Employing the neat resins containing 2.0 mol % of IOC10, the photopolymerizations were monitored using Fourier Transform real-time infrared spectroscopy (FT-RTIR). Using this technique, the disappearance of the infrared band at 886 cm$^{-1}$ due to the epoxy groups was followed as a function of time. Shown in FIG. 4 are the conversion versus time curves obtained from these studies. Included in this figure for comparison is the kinetic curve for the photopolymerization of oligomer Ib that was prepared using the process described in Scheme 1. All the epoxy functional oligomers display excellent reactivity in cationic epoxide ring-opening photopolymerization. Some structurally dependant trends can be distinguished in this study. Ib shows high reactivity as indicated by the initial portion of the kinetic curve, however, the conversion of epoxy groups reached after 200 seconds irradiation was only approximately 60%. In contrast, the photopolymerizations of all the other resins proceed to nearly quantitative conversions. It may be noted that Ib has the shortest and stiffest spacer linking the epoxycyclohexyl group with the siloxane main chain of all the resins. As a consequence, Ib would be expected to give the most highly crosslinked polymer. Despite several attempts, we were unable to measure a glass transition temperature of this polymer using DSC. This appears to be indicative of a very highly crosslinked nature. Diffusion and mobility of the bulky epoxycyclohexyl groups in such a polymer would be expected to be restricted resulting in vitrification of the polymer at low conversions.

IXb displays a relatively long induction period prior to polymerization. It is not possible to rigorously purify the oligomers after preparation and this induction period is interpreted as being due to the presence of residual basic impurities that retard the cationic ring-opening polymerization. As with Ib, no glass transition temperature was observed by DSC below 225° C. In contrast, the high mobility of the other resins with flexible siloxane groups in the spacers gives rise to much higher conversions due to suppression of the onset of vitrification.

Figure 5:
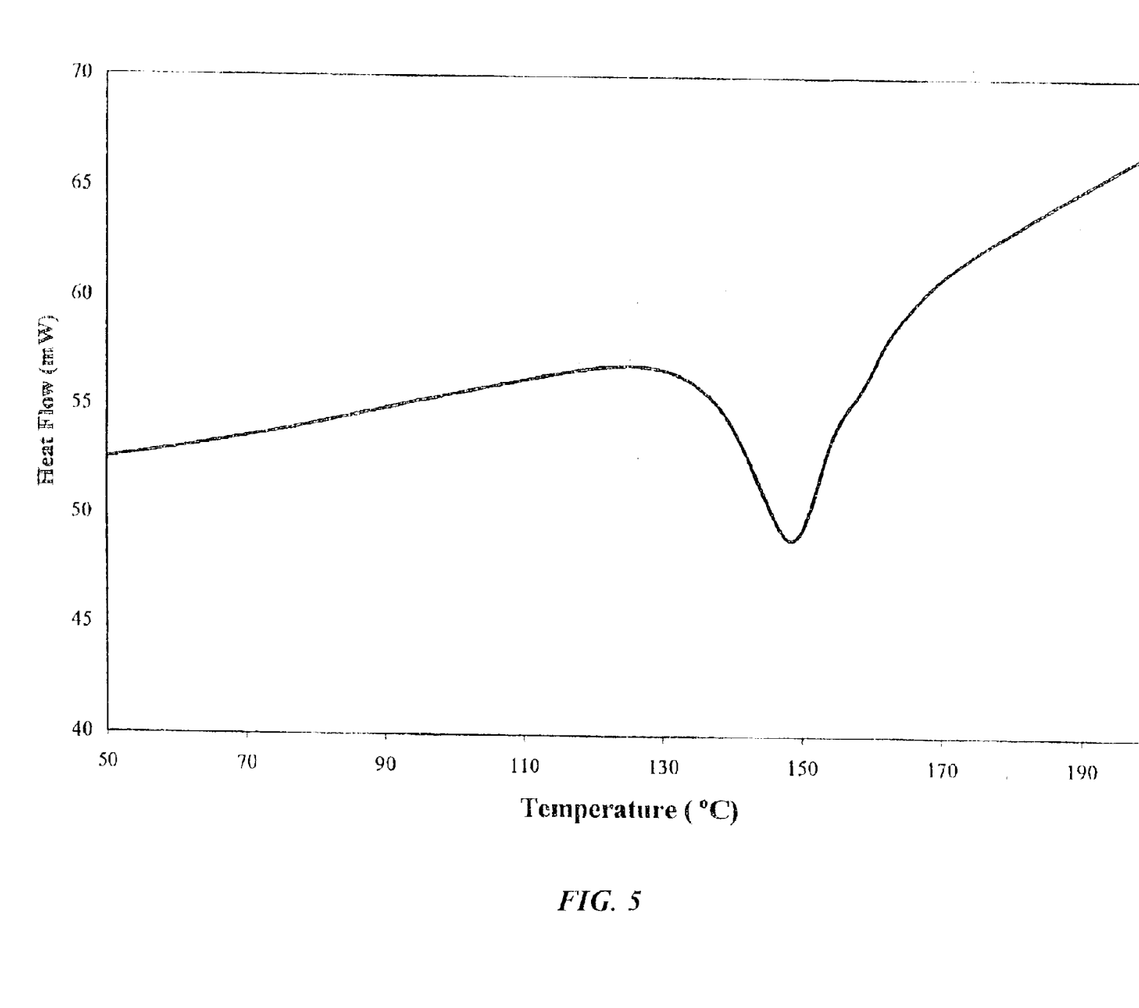
FIG. 5 shows a DSC scan of the thermally initiated cationic polymerization of silicone-epoxy oligomer VIIIb in the presence of 2.0 mol % IOC10 as initiator.

FIG. 5 shows a differential scanning calorimetric (DSC) curve for the thermal polymerization of oligomer VIIIb in the presence of 2.0 mol % IOC10. The onset of thermal decomposition of IOC10 takes place at approximately 130° C. Polymerization of this oligomer is very rapid as indicated by the sharpness of the exothermic peak in the DSC curve.

Example 8

Thermal Stability of Epoxy Functional Organic-Inorganic Hybrid Polymers

Figure 6:
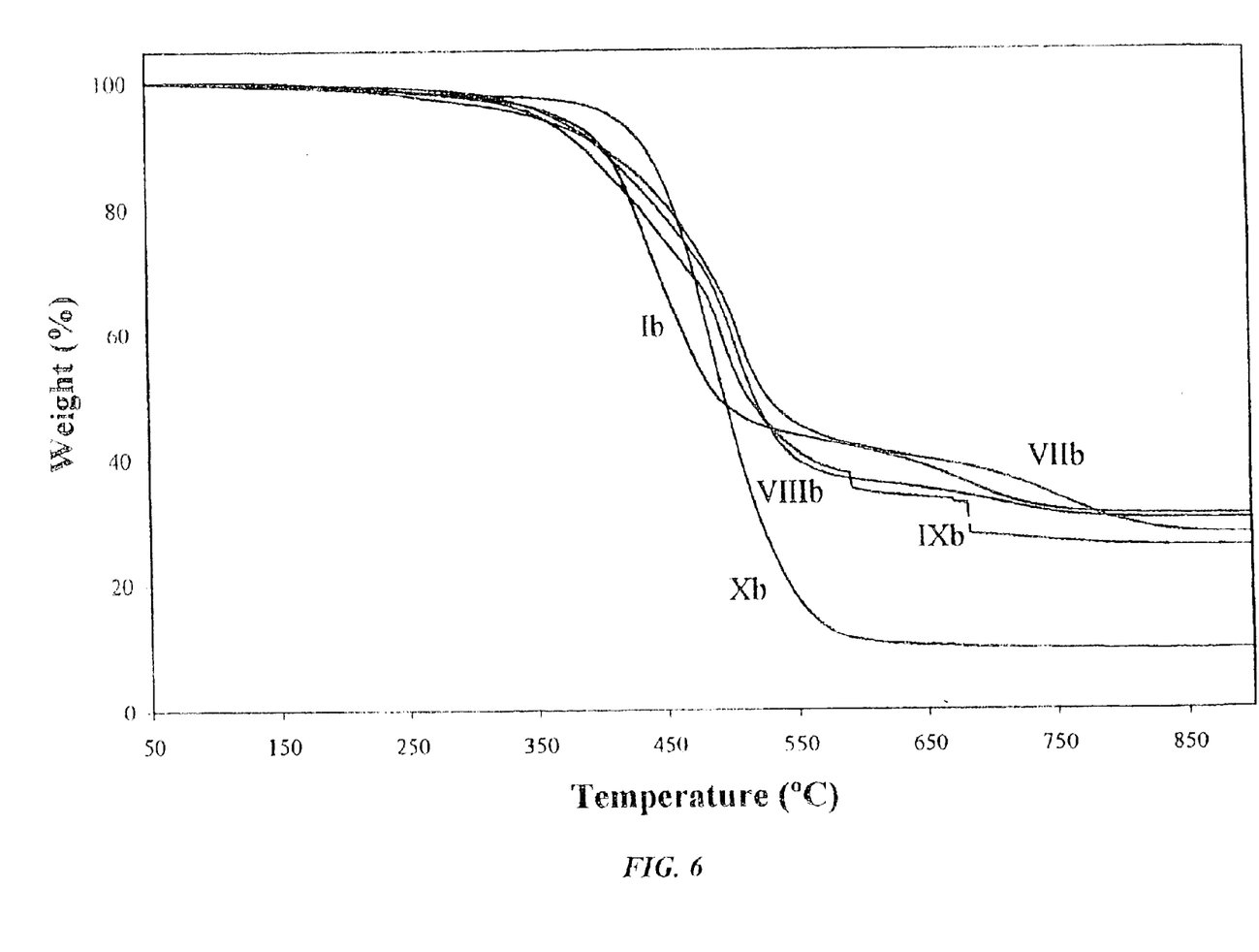
FIG. 6 is a thermogravimetric analysis study of crosslinked silicone-epoxy resins carried out at a heating rate of 20° C./min in nitrogen.

The thermogravimetric analysis (TGA) curves for thermally cured samples of the silicone-epoxy oligomers are given in FIG. 6. The TGA study was carried out in nitrogen at a heating rate of 20° C./min. The polymers display excellent stability with the onset of thermal decomposition at approximately 350-400° C. Polymer Xb bearing the longest pendant siloxane linker between the main chain and the epoxide group shows the poorest char yield probably due to cyclization and subsequent volatilization of cyclic dimethylsiloxanes formed during thermal decomposition.

Example 9

Figure 7:
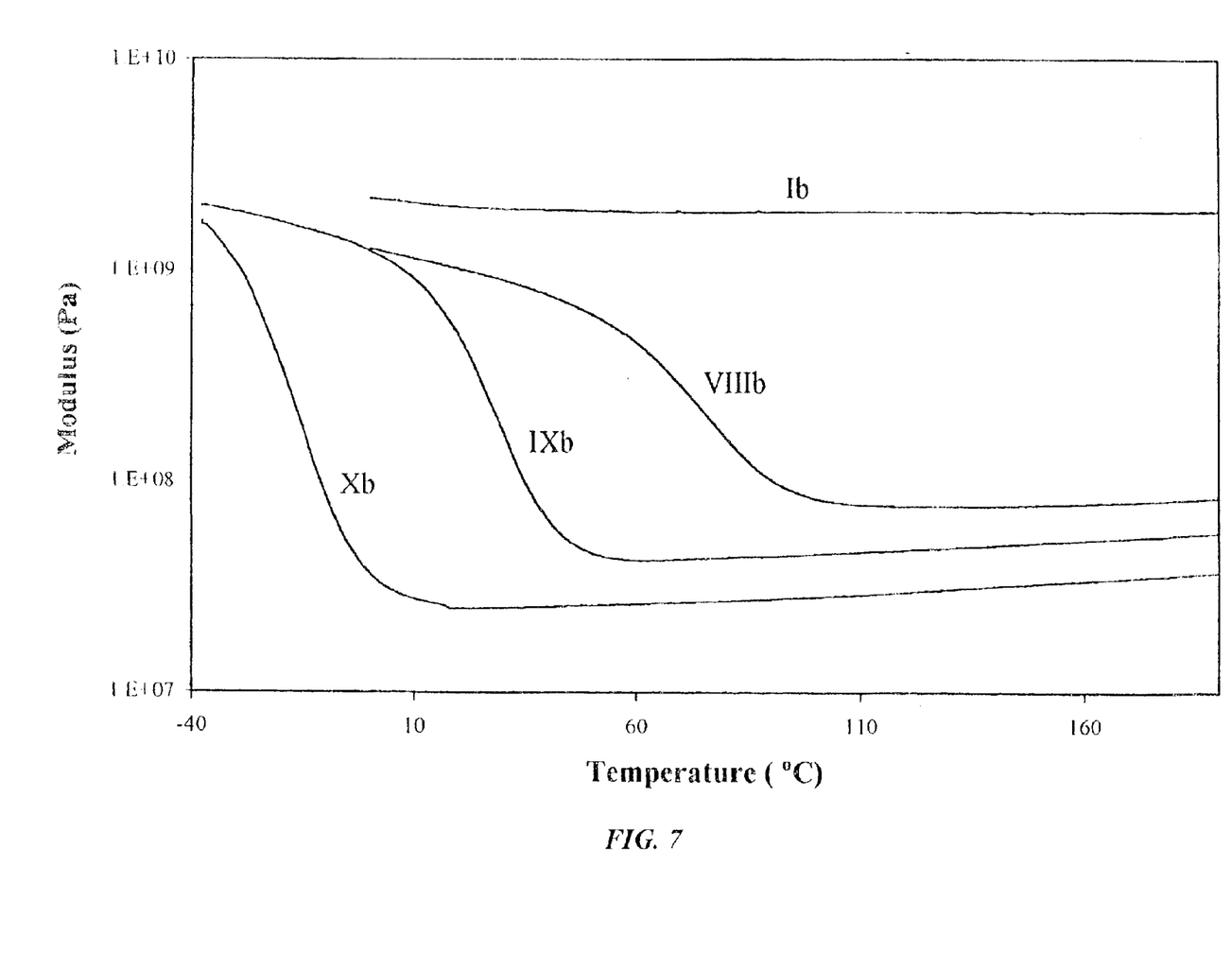
FIG. 7 shows a comparison of the storage moduli as determined by dynamic mechanical testing for thermally crosslinked silicone-epoxy resins Temperature scan rate 10° C./min in nitrogen.
Figure 8:
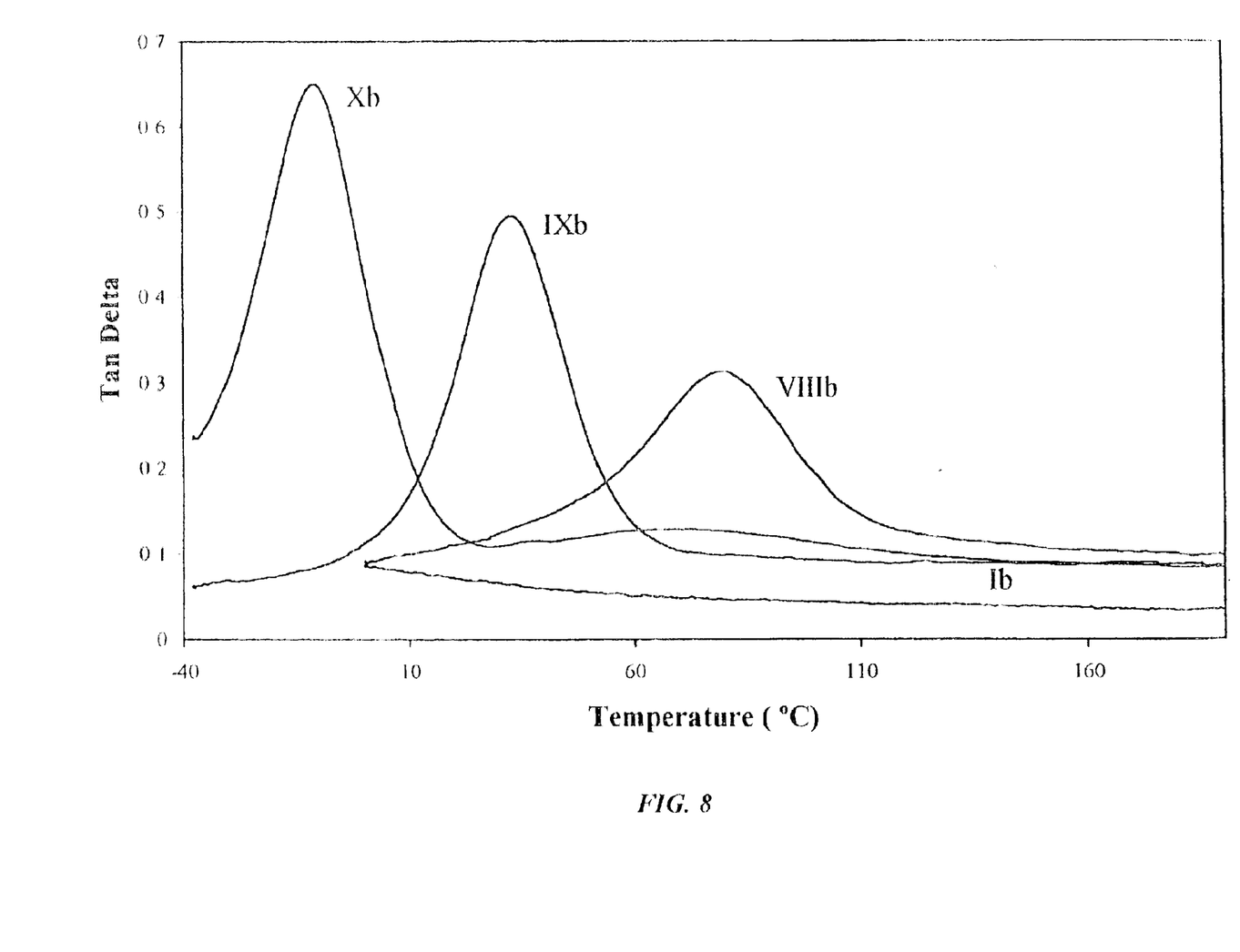
FIG. 8 is a comparison of the tan delta plots for thermally crosslinked silicone-epoxy resins under nitrogen atmosphere as determined by dynamic mechanical testing. Temperature scan rate was 10° C./min.

Mechanical Properties of Epoxy Functional Organic-Inorganic Hybrid Polymers The mechanical properties of the organic-inorganic hybrid polymers produced by thermal polymerization of the corresponding epoxy functional sol-gel oligomers were determined using dynamic mechanical analysis (DMA). The results are shown in FIGS. 7 and 8. Again, the polymer derived from Ib was included in this study for comparison. The mechanical properties of the resins are directly related to the length and type of spacer group separating the epoxycyclohexyl groups from the siloxane main chain. Accordingly, Ib would be expected to give the stiffest and highest glass transition polymer. In FIG. 7 it can be seen that this polymer exhibits no decrease in the storage modulus out to 180° C. In fact, there is no decrease in the modulus or evidence of a glass transition at temperatures below 300° C. As the length of the spacer is increased and flexible siloxane linkages are introduced, one sees a progressive decrease in the temperature of the fall off of the storage modulus that corresponds to a decrease in the glass transition temperature (FIG. 8). Polymer Xb displays the lowest glass transition temperature (−6.5° C.) while the $T_g$s for IXb and VIIIb are respectively, 33° C. and 80° C. A similar observation was made for photopolymerized thin films of these oligomers. While the film derived from Ib was brittle and could not be handled, the films from VIIIb, IXb and Xb were increasingly more flexible and tough.

What is claimed is:

1. A process for the preparation of a siloxane oligomer substituted with at least one polymerizable functional group selected from epoxy, vinyl ether, 1-propenyl ether, acrylate and methacrylate, said process comprising:

a. selectively reacting at least one compound of formula I with at least one compound chosen from A or B, to form at least one monohydrosilane or monohydrosiloxane; and b. reacting said at least one monohydrosilane or monohydrosiloxane with at least one compound chosen from A and B, to form an alkoxysilyl silane or siloxane, with the proviso that
        when A is used in step (a), B is used in step (b), and
        when B is used in step (a), A is used in step (b);

c. in the presence of an ion exchange resin, reacting 0.5 to 2.5 equivalents water and at least one alkoxysilane with the alkoxysilyl silane or siloxane, wherein the alkoxysilane is selected from alkoxysilanes of formula $SiR^6R^8R^9R^{10}$ and formula $SiR^8R^9R^{10}$ FG; and d. separating the ion exchange resin from a product of the reaction; wherein
        A is a compound containing at least one vinyl or allyl group and at least one group selected from epoxy, vinyl ether, 1-propenyl ether, acrylate and methacrylate,
        B is a compound containing at least one vinyl or allyl group and at least one dialkoxysilyl or trialkoxysilyl group;
        $R^1$–$R^4$ are independently hydrogen, alkyl, haloalkyl, arylalkyl, aryl or heterocyclic; $R^6$, $R^8$, $R^9$, and $R^{10}$ is, independently, alkyl, aryl, arylalkyl, chloroalkyl, fluoroalkyl, heteroalkyl, heteroaryl, alkoxy, arylalkoxy, chloroalkoxy, or fluoroalkoxy of 1 to 10 carbons;
        m is 0 or an integer from 1 to 3;
        n is 0 or an integer from 1 to 100; and
        FG is a linear, branched or cyclic alkyl or alkyl ether residue of 1–20 carbon atoms, or 1–20 carbon atoms and 1–9 oxygen atoms, substituted with at least one group selected from epoxy, vinyl ether, 1-propenyl ether, acrylate and methacrylate.

2. A process according to claim 1, wherein said at least one alkoxysilane is an alkoxysilane of formula $SiR^6R^8R^9R^{10}$.

3. A process according to claim 1, wherein A is used in step (a), and B is used in step (b).

4. A process according to claim 1, wherein A is selected from:

5. A process according to claim 1, wherein B is an alkoxysilane of formula II $$R^7\text{—}SiR^8R^9R^{10} \quad \text{II}$$

wherein
R$^7$ is a direct bond or a divalent aryl or alkyl residue; and
R$^8$, R$^9$, and R$^{10}$ are independently alkyl, aryl, arylalkyl, chloroalkyl, fluoroalkyl, heteroalkyl, heteroaryl, alkoxy, arylalkoxy, chloroalkoxy, or fluoroalkoxy.

6. A process according to claim 5, wherein B is selected from:

$$\text{Si(OCH}_3)_3 \quad \text{Si(OC}_2\text{H}_5)_3 \quad \text{Si(OC}_3\text{H}_7)_3$$

$$\text{CH}_2\text{Si(OCH}_3)_3 \quad \text{CH}_2\text{SiPh(OCH}_3)_2$$

$$\text{SiPh(OCH}_3)_2 \quad \text{Si(OCH}_3)_3$$

$$(\text{CH}_2)_4\text{Si(OCH}_3)_3 \quad (\text{CH}_2)_6\text{Si(OCH}_3)_3.$$

7. A process according to claim 1, wherein A is 3-vinyl-7-oxabicyclo[4.1.0]heptane.

8. A process according to claim 1, wherein B is vinyl trimethoxysilane.

9. A process according to claim 1, wherein R$^1$–R$^4$ is methyl and n is 1–3.

10. A process according to claim 1, wherein I is 1,1,3,3-tetramethyldisiloxane.

11. A process according to claim 1, wherein I is 1,1,3,3,5,5-hexamethyltrisiloxane.

12. A process according to claim 1, wherein I is 1,1,3,3,5,5,7,7-octamethyltetrasiloxane.

13. A process according to claim 1, wherein I is methylphenylsilane.

* * * * *